(12) United States Patent
Wright et al.

(10) Patent No.: US 6,552,800 B1
(45) Date of Patent: *Apr. 22, 2003

(54) SINGLE-ARM SAGNAC INTERFEROMETER WITH TWO BEAM SPLITTERS

(75) Inventors: Oliver B. Wright, Sapporo (JP); David H. Hurley, Kalispell, MT (US); Osamu Matsuda, Sapporo (JP)

(73) Assignee: Japan Science and Technology Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/890,437

(22) PCT Filed: Jun. 21, 2000

(86) PCT No.: PCT/JP00/04033

§ 371 (c)(1),
(2), (4) Date: Jul. 31, 2001

(87) PCT Pub. No.: WO01/61323

PCT Pub. Date: Aug. 23, 2001

(30) Foreign Application Priority Data

Feb. 17, 2000 (JP) ........................................ 2000-038981

(51) Int. Cl.[7] .............................................. G01N 21/00
(52) U.S. Cl. ........................ 356/497; 356/502; 73/655
(58) Field of Search ................................ 356/432, 502, 356/485, 486, 492, 497; 73/655, 657

(56) References Cited

U.S. PATENT DOCUMENTS

| 5,706,094 A | 1/1998 | Maris | 356/432 |
| 6,008,906 A | * 12/1999 | Maris | 250/226 |
| 6,323,951 B1 | * 11/2001 | Borden et al. | 356/502 |

FOREIGN PATENT DOCUMENTS

| JP | 04009641 A | 1/1992 |
| JP | 05172739 A | 7/1993 |
| JP | 11-511240 | 9/1999 |

* cited by examiner

Primary Examiner—Stephone B. Allen
Assistant Examiner—Bradford Hill
(74) Attorney, Agent, or Firm—Lorusso, Loud & Kelly

(57) ABSTRACT

The invention provides an apparatus for measuring the physical properties of a sample by optically monitoring the response of the sample to illumination by ultrashort optical pulses. The apparatus is a common path optical interferometer of a Sagnac type that can measure physical properties at normal incidence, i.e., a single-arm Sagnac interferometer featuring two beam splitters. Measurement is performed in such a manner that a sample is excited by a beam of ultrashort optical pulses, and variations in intensity and phase of another optical beam are detected. This enables a wide range of measurement of physical properties such as thickness, sound velocity, and thermal properties of substances.

37 Claims, 8 Drawing Sheets

ANGLE OF QUARTER WAVE PLATE (Ψ)

ANGLE OF QUARTER WAVE PLATE (Ψ)

ANGLE OF QUARTER WAVE PLATE (Ψ)

SINGLE-ARM SAGNAC INTERFEROMETER WITH TWO BEAM SPLITTERS

TECHNICAL FIELD

The present invention enables the on-line measurement of semiconductor wafers or integrated circuits with high lateral resolution. In particular, the invention can be used to estimate the thickness profile of a sample consisting of a multilayer thin film on a substrate. The invention can also be used to estimate thermal properties of a sample, or quantities that influence these properties such as the ion implantation dose in semiconductor wafers. Moreover, the present invention can determine properties of a sample non-destructively and without contact with the sample, and can be used in on-line conditions on product wafers.

There are also many other possible industrial applications of the present invention. Whenever thin films or layers are deposited on a sample, or whenever properties of a sample need to be measured on short length scales, this invention can provide a wide range of information about the physical properties of the sample, such as mechanical or thermal properties crucial to the performance of the final product.

BACKGROUND ART

The non-destructive measurement of physical properties on micron, sub-micron, or nanometer length scales with optical techniques has been proposed in a wide variety of contexts.

For example a method for measuring the thickness or sound velocity of micron or sub-micron thin films has been proposed by J. Tauc et al. (see the specification of U.S. Pat. No. 4,710,030). This relies on the excitation of short wavelength stress pulses in a sample with ultrashort duration pump optical pulses and the detection of stress-induced changes in the optical constants of the sample using delayed probe optical pulses, in particular by measuring the changes in intensity of the probe beam reflected from the sample.

However, this method fails when the optical constants of the sample do not vary significantly with stress or strain in the sample at the wavelength of light used.

A similar method, that can be used to get round this limitation, was proposed by O. B. Wright and K. Kawashima (see Phys. Rev. Lett. vol. 69, 1668–1671 (1992)). It is based on the angular deflection of a probe beam arising from surface motion. Stress or strain pulses are always, accompanied by motion of the sample surface or sample interfaces, and so this method can also be used to measure the thickness or sound velocity of thin films. This method, simultaneously sensitive to both phase and intensity changes in the light reflected from the sample, requires that the ultrashort optical pump and probe beams should be focused to slightly different positions at the sample surface. However, this method has the disadvantage of being very sensitive to the alignment of the pump and probe beams, in particular to the pump and probe optical spot separation on the sample. Moreover, the resolution is limited by the pointing stability of the laser used and by mechanical vibrations.

Another related method to generate and detect stress pulses with ultrashort optical pulses, proposed by T. F. Crimmins et al. (see Appl. Phys. Lett. vol. 74, 1344–1346, 1999) and H. J. Maris et al. (U.S. Pat. No. 5,864,393), relies on a grating technique making use of two pump beams at oblique incidence. This method, simultaneously sensitive to both phase and intensity changes in the light reflected from the sample, requires that two pump beams are simultaneously focused to the same spot on the sample at non-normal incidence.

However, measurements at normal incidence are highly desirable because the spots are circular and also because a single microscope objective can then be used to focus all the optical beams onto the sample, facilitating alignment and the obtention of a small optical spot size. Moreover, this grating technique requires several optical fringes to be produced on the sample at the same time, and this constitutes another reason why the method is not suitable for the highest lateral resolution measurements with the smallest optical spot sizes.

Another example of the use of optical techniques for the measurement of physical properties on short length scales is the use of thermal waves in the measurement of film thickness or ion implantation dose. A. Rosencwaig et al. (see Appl. Phys. Lett., vol. 46, 1013–1015, 1985), W. L. Smith et al. (see Nucl. Instrum. and Methods Phys. Res. Sect B, vol. B21, 537–541, 1987) and J. Opsal et al. (see U.S. Pat. No. 5,074,669) propose using chopped CW light beams to periodically excite thermal waves in a sample and to probe the resulting change in optical constants with a probe beam. This method can be used to probe to depths into the sample to within the thermal diffusion length, and is typically used for probing up to chopping frequencies in the 10 MHz region. However, at higher frequencies above 1 GHz, the method becomes impractical because the periodic temperature changes, dependent on the energy deposited in the sample by the excitation beam in one chopping cycle, decrease rapidly with increasing frequency. Higher frequency measurements are useful, because the thermal diffusion length, proportional to $1/\sqrt{f}$ (f the chopping frequency), becomes smaller and the signals then become more sensitive to thermal properties of the sample in the near-surface region. When films of nanometer order in thickness are deposited on a substrate, it is, however, desirable to use such higher frequencies or equivalent short time scale pulsed optical measurements. Such short time scale pulsed optical measurements were proposed by C. A. Paddock and G. Eesley (see Opt. Lett., vol. 11, 273–275, 1986) using ultrashort pump and probe optical pulses. By monitoring the changes in optical intensity of a probe pulse reflected from the sample, it was possible to obtain a measure of the temperature change of the sample in the near-surface region in response to a pump pulse, and from the characteristic decay time of this temperature change estimate the thermal diffusivity of the sample. However, this method relies on the coupling of the optical reflectivity of the sample to temperature changes. If the optical reflectivity of the probe beam does not depend significantly on the temperature changes of the sample, the method fails.

Many optical interferometers have been proposed to measure the ultrafast changes in the properties of a sample in response to excitation by optical pulses on picosecond time scales. Such measurements have the advantage of being simultaneously sensitive to both phase and intensity changes in the light reflected from the sample, allowing a maximum of information to be extracted. If the optical reflectivity does not depend significantly on temperature or stress, there remains the possibility of monitoring temperature changes or the presence of stress pulses from changes in the optical phase. In addition, interferometric techniques are very sensitive, and interferometers can be easily calibrated to give quantitative information about, for example, the amplitude of the motion of the sample surface.

One example of an interferometric technique is time-division interferometry, in which an ultrashort optical probe pulse and an ultrashort optical reference pulse separately interact with a sample. For example, if the reference pulse is set to always arrive before a corresponding pump pulse and the probe pulse is set to always arrive after a corresponding pump pulse, the effect of the pump pulse on the sample can be determined by interfering the probe and reference pulses at a detector. Such a configuration, based on a Mach-Zehnder interferometer, was proposed by L. Sarger et al. (see J. Opt. Soc. Am. B, vol. 11, 995–999, 1994). This interferometer was designed for measurements in transmission through a sample. The Mach-Zehnder configuration is not a common path configuration, because it requires the probe and reference beams to travel completely different optical paths. It is thus is susceptible to unwanted noise sources such as mechanical vibrations or temperature changes.

Another configuration based on a Sagnac interferometer was proposed by M. C. Gabriel et al. (see Opt. Lett., vol. 16, 1334–1335, 1991) for measurements in transmission through a sample. This time-division interferometer is common path and is thus very stable with respect to mechanical vibrations or temperature changes. The same configuration could be used for measurements in reflection from a sample by placing the sample in the place on one of the mirrors in the Sagnac ring. However, it is not suitable for measurements at normal incidence. Moreover, the theory for the response of samples to ultrashort optical pulse excitation is simplified for the case of probing at normal incidence, rendering the data analysis much easier.

Another configuration based on a Sagnac interferometer was proposed by M. J. LaGasse et al. (see Appl. Phys. Lett., vol. 54, 2068–2070, 1989) for measurements in transmission through a sample. However this configuration is also not suitable for measurements at normal incidence. Moreover, this configuration is not suitable for opaque samples.

Another configuration based on a Michelson interferometer was proposed by J. Fieldler and J. W. Wagner (see Rev. Prog. Quant. Nondestr. Eval., vol. 16, 1579–1584, 1997) and C. J. K. Richardson et al. (see J. Opt. Soc. Am. B, vol. 16, 1007–1015, 1999) to monitor stress pulses in a sample generated with ultrashort optical pump pulses. This configuration is relatively stable but is, however, not suitable for measurements at normal incidence. Moreover, the probe and reference beams are not incident on the same point on the sample, and so errors can arise when lateral variations in optical reflectivity of the sample are present.

Another configuration based on a Michelson interferometer was proposed by O. B. Wright (Japan Patent Application Laid-Open (kokai) No. 5-172739, Jul. 9, 1993) to monitor stress pulses in a sample generated with ultrashort pump optical pulses through, in particular, the effect of stress-induced surface vibrations on the optical phase. This Michelson configuration does allow measurement at normal incidence. However the design is not common path. It is thus susceptible to unwanted noise sources such as mechanical vibrations or temperature changes.

Sagnac interferometers have also been designed for use with CW light beams. An example of this is disclosed in the U.S. Pat. No. 5,894,531 (J. J. Alcoz). The basic elements of the interferometer, making use of two arms and two beam splitters, is suitable for measurements at normal incidence and for detecting ultrasonic waves. However, working with CW light beams is not suitable for measurements on short time scales, in particular on picosecond time scales. This approach is therefore not suitable for the investigation of the physical properties of the sample on short length scales in the direction perpendicular to the sample surface.

Methods proposed by H. J. Maris (U.S. Pat. Nos. 5,706,094, 5,864,393) and by H. J. Maris and R. J. Stoner (U.S. Pat. Nos. 5,748,317, 5,748,318, 5,844,684 and 5,959,735) involve refinements of the original method by J. Tauc et al. (U.S. Pat. No. 4,710,030) for the monitoring of physical properties of materials. These methods involve the use of ultrashort optical pulses for the measurement of mechanical and thermal properties through, for example, variations in optical reflectivity and optical phase.

However, the methods described in these patents that are sensitive to optical phase variations; i.e., the beam deflection technique and the grating technique, are not suitable for the highest lateral spatial resolution measurements involving both pump and probe pulses focused to diffraction limited spots. The beam deflection technique, as previously mentioned, requires an offset between the pump and probe pulses and hence results in a degradation in lateral resolution.

In addition, the stability of the beam deflection technique is limited by the pointing stability of the laser used and by mechanical vibrations. The other method, the grating technique, requires several optical fringes to be produced on the sample at the same time using two pump beams at oblique incidence. For the reasons already explained above this technique is not suitable for measurements with the highest lateral spatial resolution.

One more proposed method in these patents and by O. B. Wright (Proceedings of the Ultrasonics Symposium, 1995, pp. 567–575) involves obtaining a better resolution than the diffraction limit using optical near-field techniques, such as the use of a tapered optical fiber. However, this method, because of the small aperture involved, implies the use of very low levels of optical power, and it therefore has the disadvantage of a much degraded signal-to-noise ratio.

DISCLOSURE OF THE INVENTION

As described above, conventional apparatuses for measuring physical properties of samples have various problems.

In the present invention, the measurement of properties of materials on short length scales, from 0.1 nm to 100 $\mu$m, can be achieved by the use of short optical pulses, typically from 0.01 ps to 1 ns in duration, to monitor changes in physical properties of a sample induced by pump optical pulses, such as the generation and propagation of short wavelength stress pulses or thermal waves.

The effective measurement of such changes in physical properties of a sample with high stability using short optical pulses requires a simple and robust apparatus. In order to be able to apply the technique to a wide range of samples it is advantageous to use interferometry, inherently simultaneously sensitive to both phase and intensity changes of light reflected from the sample, allowing a maximum of information to be extracted. In order to obtain high spatial resolution, stability and to simplify the data analysis, it is advantageous to use a single lens at normal incidence to monitor the ultrafast changes in physical properties of a sample induced by pump optical pulses. This configuration is also desirable from the point of view of improved lateral resolution because the pump and probe light can be focused to a diffraction limited circular spot. At the same time it is highly desirable to use a common path design in order to minimize the effects of spurious mechanical vibrations or temperature changes.

The present invention provides an apparatus for measuring physical properties of a sample based on the use of ultrashort optical pulses that aims to satisfy all these requirements simultaneously.

An object of the present invention is to provide an apparatus for measuring the physical properties of a sample by optically monitoring the response of the sample to illumination by ultrashort optical pulses.

Another object of the invention is to provide such an apparatus that does not make mechanical contact with the sample and that can be non-destructive.

Still another object of the invention is to provide such an apparatus that can measure physical properties of the sample on short length scales in the direction perpendicular to the sample surface.

Still another object of the invention is to provide an apparatus that can measure physical properties of a sample with a horizontal resolution of the order of 1 micron or less. The lower limit of the resolution is determined only by the optical diffraction limit.

Still another object of the invention is to provide such an apparatus that can measure physical properties of a sample by optically monitoring the response of the sample to illumination by ultrashort optical pulses using a design that allows measurements that are simultaneously sensitive to both phase and intensity changes of the light reflected from the sample and, at the same time, allows measurements that are limited in lateral resolution only by the optical diffraction limit with a circular spot.

Still another object of the invention is to provide such an apparatus that can measure physical properties of a sample by optically monitoring the response of the sample to illumination by ultrashort optical pulses using a design that is insensitive to the effects of spurious mechanical vibrations or temperature changes.

Still another object of the invention is to provide such an apparatus that can measure physical properties of a sample by optically monitoring the response of the sample to illumination by ultrashort optical pulses with the optical measurement beam incident on the sample at normal incidence, in order to facilitate data analysis, alignment and the obtention of a high lateral resolution.

Still another object of the invention is to provide such an apparatus that can measure physical properties of a sample by optically monitoring the response of the sample to illumination by ultrashort optical pulses, in which diffraction limited light is focused in a circular region on the sample, in order to obtain a high lateral resolution.

Still another object of the invention is to provide such an apparatus in which it is possible to arrange in addition for both the pump and measurement beams to be incident on the sample at normal incidence using the same means for focusing for both.

Still another object of the invention is to provide such an apparatus that can spatially map the sample in the lateral direction and can measure physical properties of the sample corresponding to in the in-plane direction in the sample.

Still another object of the invention is to provide such an apparatus that can measure stress pulses generated by an optical pump pulse in samples without the requirement of a variation of the optical constants with stress.

Still another object of the invention is to provide such an apparatus that can measure temperature changes in samples without the requirement of a variation of the optical constants of the sample with temperature.

Still another object of the invention is to provide such an apparatus that can measure physical properties of very thin films.

Still another object of the invention is to provide such an apparatus that can measure samples consisting of one or more layers or consisting of a material with a buried permanent inhomogeneity or inhomogeneities.

Still another object of the invention is to provide such an apparatus that can measure samples made up of opaque, transparent or semitransparent parts or a combination of these.

In order to achieve the above-objects, the present invention provides an apparatus which can measure the maximum amount of information about the optical response of a sample on short length scales when illuminated by ultrashort optical pulses, while at the same time satisfying the requirements for insensitivity to the effects of spurious mechanical vibrations or temperature changes and the requirement for high lateral spatial resolution down to the optical diffraction limit, ease of alignment, and ease of data analysis.

This invention features an optical generation and detection system for measuring the physical properties of a sample. There is a coherent or partially coherent radiation source for providing a pulsed measurement beam usually consisting of a periodic train of ultrashort optical pulses, having a duration of 0.002 ps to 2 ns. A typical example of such a radiation source is a mode-locked solid-state laser of high repetition rate.

There is also a radiation source for providing a pump beam usually consisting of a periodic train of ultrashort optical pulses, usually derived from the same radiation source as the measurement beam, having a duration of 0.002 ps to 2 ns.

The interferometer section of the apparatus is based on a Sagnac design. The interferometer section of the apparatus features two beam splitters used for the measurement beam. The first beam splitter directs the measurement beam to a second beam splitter. Part of the measurement beam, when incident on the second beam splitter, is split into a probe beam that travels in the single arm of the interferometer. The word 'arm' here refers to a path in the interferometer that is traversed by the reference and probe pulses at distinct different times.

This probe beam is recombined with the remaining part of the measurement beam split from the second beam splitter, known as the reference beam. A recombined beam is formed containing the reference beam and the probe beam of different states of polarization. The optical path length of the arm is chosen to be longer than the spatial extent, in the direction of propagation of the light, of the optical pulses in the reference and probe beams. Equivalently, the length of the arm $\Delta L$ is chosen in general to be longer than $c\Delta t$, where c is the speed of light in the medium of the arm and $\Delta t$ is the duration of the optical pulses making up the probe or reference beams.

This recombined beam is directed onto the sample at normal incidence, passing, for example, through a quarter wave plate and a focusing lens. This recombined beam is reflected from the sample. When reflected from the sample it is the reference beam that travels in the single arm of the interferometer in the opposite direction to that previously mentioned for the probe beam when it travels through the single arm. The reference beam and the probe beam are recombined at the second beam splitter to produce a returning measurement beam propagating in the opposite direction to that of the measurement beam when the measurement beam is initially incident on the second beam splitter. This returning measurement beam then traverses the first beam splitter to produce a first output beam containing the reference and probe beams separate from the measurement beam.

A means for introducing a known phase difference between corresponding optical pulses in the reference beam and the probe beam at a photodetector is used, typically a quarter wave plate placed in the path of the first output beam or before the first beam splitter. The known phase difference is chosen to be not equal to 0±180I degrees, where I is an integer; in order to ensure that the measurements are simultaneously sensitive to changes in both the phase and the intensity of the light reflected from the sample.

The phase difference between the probe and reference beams is typically chosen to be ±90 degrees. This first output beam then passes through a linear polarizer. The probe and reference beams, or part of them, then interfere at a photodetector or photodetectors. The signal or signals from these photodetectors are representative of the changes induced in the sample by the pump beam. Because the probe and reference beams travel along identical optical paths, apart from the small time interval representing the optical transit time through the system, the interferometer is common path and insensitive to spurious mechanical vibrations or temperature changes.

A pump beam is directed onto the sample from a chosen direction, that can be collinear with the probe and reference beams when incident on the sample. The intervals in arrival times between the pump, probe and reference pulses can be chosen or varied at will, to produce measurements as a function of these time intervals.

The illuminated region of the sample can be scanned over the sample, or the region illuminated by the probe and reference beams can be scanned with respect to the region illuminated by the pump beam, in order to spatially map the signal or signals simultaneously dependent on ultrafast changes in both phase and intensity of the light reflected from the sample.

The optical pulses comprising the pump beam excite, in general, carriers, temperature changes and stress pulses in the sample. These stress pulses can be, for example, longitudinal waves, shear waves, surface waves or interface waves, including, for example, Lamb waves, Rayleigh waves, Love waves or Stoneley waves. These carriers, temperature changes or stress pulses give rise to mechanical motion of the surface of the sample or of interfaces in the sample and also to changes in optical constants of the sample. The purpose of the present invention is to provide an improved system for measurements that are simultaneously sensitive to both phase and intensity changes of the light reflected from the sample, and hence to monitor signals related to the changes induced by the pump beam. These signals can be analyzed to determine physical properties of the sample such as thickness, sound velocity, elastic constants or thermal properties, or quantities that influence these properties such as ion implantation dose.

It is also possible to monitor ejectant from the sample or irreversible transformation of the sample in the case when the optical pulses interact with the sample destructively, and to use this, for example, to measure the plasma dynamics or other parameter of the irreversible transformation.

BEST MODE FOR CARRYING OUT THE INVENTION

Figure 1:
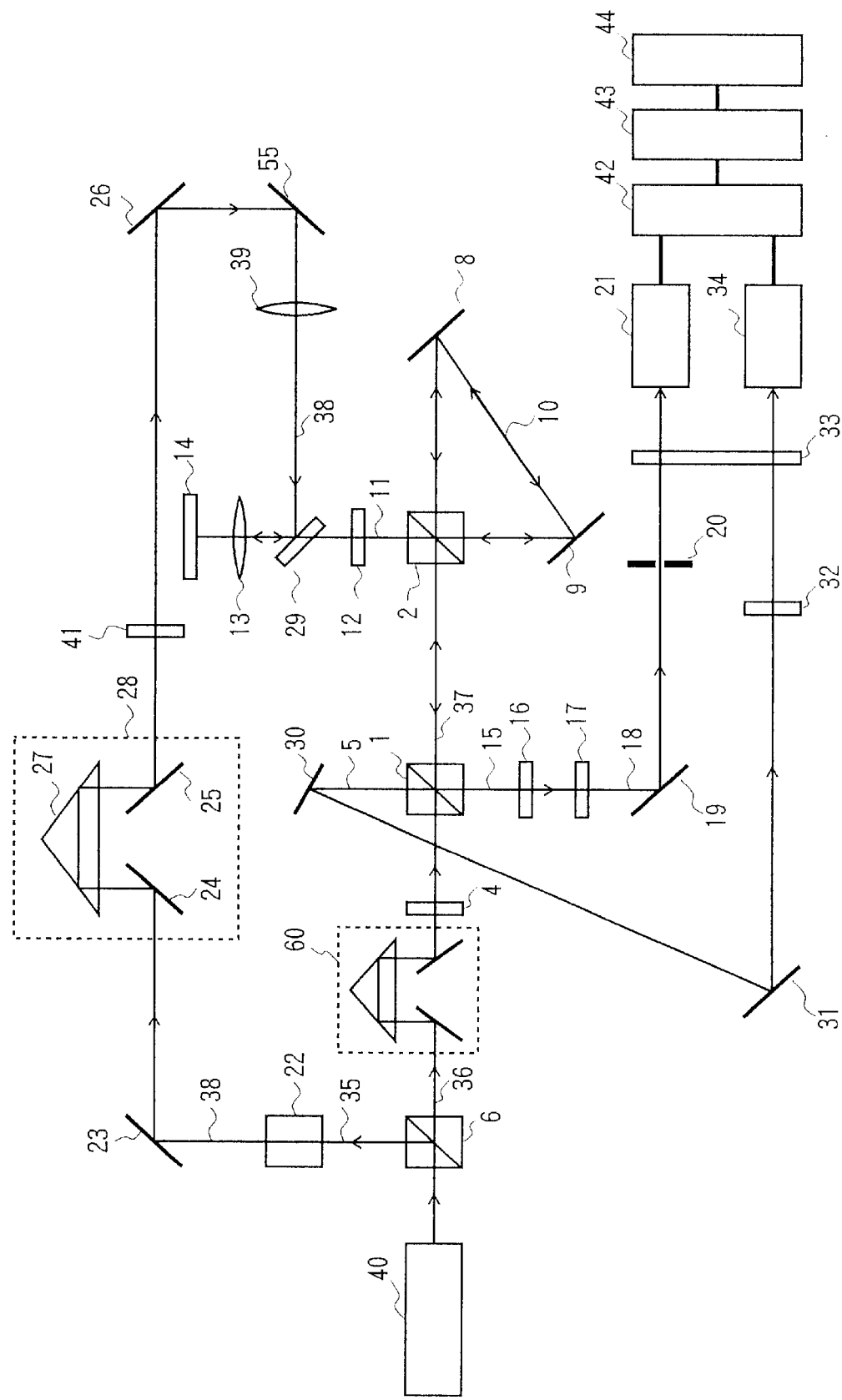
FIG. 1 is a diagram showing the configuration of a sample measurement apparatus according to a first embodiment of the invention, which apparatus uses a single-arm interferometer with two beam splitters. The pump beam has a different wavelength from the measurement beam, and the measurement beam sampling beam is used to improve the signal-to-noise ratio. The quarter wave plate and polarizer combination in the first output beam are used to achieve maximum phase sensitivity.

FIG. 1 is a diagram showing the configuration of a sample measurement apparatus according to a first embodiment of the invention, which apparatus uses a single-arm interferometer with two beam splitters.

The optical output of a coherent or partially coherent radiation source 40, producing a periodic train of short optical pulses, is split by a beam splitter 6 into two beams, a beam 35 and a measurement beam 36. The measurement beam 36 is then passed through a delay line 60, and through a polarizer 4 aligned with its axis at 45 degrees to the plane of the figure.

After this a beam splitter (first beam splitter) 1, chosen in this embodiment to be a 50/50 non-polarizing beam splitter, is placed in the path of the measurement beam 36. This initially samples a portion of the measurement beam 36, the measurement beam sampling beam 5, that can be used later in a differential detection scheme to improve the signal-to-noise ratio. The remaining portion of the measurement beam 36 is incident on a second beam splitter 2, chosen to be a polarizing beam splitter. The measurement beam 36 is thereby split into two beams of perpendicular linear polarization, one of horizontal polarization and one of vertical polarization with respect to the plane of FIG. 1, the probe beam and the reference beams, respectively. The probe beam travels in the single arm 10 of the interferometer containing mirrors 8 and 9. This probe beam is recombined with the remaining part of the measurement beam 36 split from the second beam splitter 2, known as the reference beam. A recombined beam 11 is formed containing the reference beam and the probe beam. The axes of the beam splitters 1 and 2 are arranged to be parallel.

This recombined beam 11 passes through a first quarter wave plate 12 with its axes at 45 degrees to those of the second beam splitter 2 so that both the probe and reference beams are converted to circular polarization. The recombined beam 11 passes through a means for focusing 13 that can be chosen to be a high power microscope objective, and then is focused on the sample 14 at normal incidence. This recombined beam 11 is reflected from the sample 14, passing back through the same means for focusing 13. On passing through the first quarter wave plate 12 a second time the probe and reference beams revert to linear polarizations perpendicular to those they had before passing the first time through this first quarter wave plate 12.

After reflection from the sample 14 it is therefore the reference beam that travels in the single arm 10 of the interferometer in the opposite direction to that previously mentioned for the probe beam when it travels through the single arm 10. The reference beam and the probe beam are recombined at the second beam splitter 2 to produce a returning measurement beam 37 propagating in the opposite direction to that of the measurement beam 36 when the measurement beam 36 is initially incident on the second beam splitter 2. This returning measurement beam 37 then traverses the first beam splitter 1 to produce a first output beam 15 containing the reference and probe beams separate from the measurement beam 36.

This first output beam 15 then passes through a second quarter wave plate 16 aligned with its axes parallel to the axes of the first beam splitter 1, and hence parallel to those of the probe and reference beam linear polarizations. This second quarter wave plate 16 can also be placed at the input side of the interferometer, between polarizer 4 and the first beam splitter 1. This waveplate introduces a phase difference of ±90 degrees between the probe and reference beams, the exact phase difference depending on whether the fast or slow axis of the second wave plate 16 corresponds to the probe or reference polarization. After this the first output beam 15 passes through a linear polarizer 17 with its axes aligned at an angle of 45 degrees to those of the second quarter wave plate 16. The second output beam 18 is then guided by mirror 19 and passes through a spatial filter 20, such as an adjustable aperture, that can be used to select a portion of the interference pattern if necessary to improve the contrast of the interferometer. The probe and reference beams are then made to interfere at a photodetector 21.

In this embodiment the pump beam 38 of different central wavelength from the measurement beam 36 is produced by passing beam 35 through nonlinear crystal 22 that doubles the optical frequency of the beam to produce the second harmonic. Mirrors 23, 24, and 55 guide the pump beam 38 into an optical delay line 28 containing a corner cube 27. This delay line is used to adjust the interval in arrival time at the sample between optical pulses comprising the pump beam 38 and corresponding optical pulses comprising the probe and reference beams. Mirrors 25 and 26 then guide the pump beam 38 to a dichroic beam splitter 29 that combines the pump beam 38 with the recombined beam 11. The same means for focusing 13 is used for the pump beam 38. If required an extra focusing element 39 can be introduced to ensure that the pump beam 38 and recombined beam 11 are both optimally focused with a small spot size on the sample 14 in the case when the means for focusing 13 exhibits chromatic aberration or when the pump beam 38 and recombined beam 11 diameters or beam divergences are different. In this embodiment the pump beam 38 and recombined beam 11 are focused to the same point on the sample. This embodiment can be used for measuring, for example, the propagation of stress pulses or thermal waves in the through-thickness direction of the sample.

In this embodiment the measurement beam sampling beam 5 is obtained by the reflection of the measurement beam 36 from the first beam splitter 1. This measurement beam sampling beam 5 is guided by mirrors 30 and 31 through a variable attenuator 32 to photodetector 34. The filter 33 prevents any light at the pump beam wavelength from reaching either photodetector. The variable attenuator 32 is adjusted so that equal powers arrive at each photodetector 21, 34. The signals from the photodetectors 21 and 34 are subtracted using a circuit 42 to produce an output signal to reduce the effect of fluctuations in the intensity of the measurement beam, and so improve the signal-to-noise ratio.

In this embodiment the intensity of the pump beam 38 is modulated by a chopper 41. The output signal from the circuit 42 is fed to a lock-in amplifier 43 tuned to the modulation frequency, and the lock-in amplifier 43 produces a signal proportional to the amplitude of the modulated component of the output signal from the circuit 42 which has the same frequency as the modulation frequency of the pump beam 38. The output of the lock-in amplifier 43 is fed to a signal averager 44, to give a final signal representative of the simultaneous ultrafast changes in both phase and intensity of the light reflected from the sample 14. This modulation technique is well known in the art of ultrashort pulse optical pump and probe techniques.

As is also well-known in the art of optical signal processing, sampling beams proportional to the pump beam and measurement beam intensities can be monitored and used in a compensation system. That is, the input or output signal of the lock-in amplifier 43 can be divided by these signals in order to reduce the effect of the intensity fluctuations in the pump beam or measurement beam on the lock-in amplifier output signal.

Also, using methods well known in the art, it is also possible to monitor the measurement beam optical intensity both before and after reflection from the sample in order to compensate for changes in the average sample reflection coefficient at the measurement beam wavelength. This would be useful, for example, if the sample is scanned laterally. One particular method for avoiding the problem of the change in average sample reflection coefficient at the probe beam wavelength, for example, is to feed a signal proportional to the output of photodetector 21 through a low pass filter to control the gain of photodetector 34 so that the average dc outputs of the two photodetectors are equal.

In this embodiment it is arranged for each pump pulse to arrive between each corresponding probe and reference pulse, so that the role of the reference pulse is to probe the state of the sample before the arrival of the pump pulse whereas the role of the probe pulse is to probe the state of the sample after the arrival of the pump pulse. This order of pump, probe and reference pulses is conventionally used in time division interferometers, although other orders are possible.

The interferometer is very stable and straightforward to align. Even with deviations from alignment, operation is still possible. For example the interferometer will also work with slight deviations from normal incidence on the sample 14 of the recombined beam 11.

The theory of operation of the interferometer for this embodiment is as follows. As a concrete example, the input polarization of the measurement beam 36 after passing through polarizer 4 is taken to be oriented at 45° in the direction $\hat{x}-\hat{y}$ where the coordinate unit vectors $\hat{x}$, $\hat{y}$ and $\hat{z}$ are defined so that z is always the beam propagation direction and y is the upward out-of-plane direction in FIG. 1. The polarizer 17 is chosen with transmission axis aligned at 45° in the direction $\hat{x}+\hat{y}$. Just after reflection from the first beam splitter 1 the electric field of the first output beam 15 can be expressed as the Jones vector (Er'$\hat{x}$–Er$\hat{y}$), where r is the complex amplitude reflection coefficient of the sample 14 seen by the reference beam and r' is that seen by the probe beam. The quantity r' depends on the interval in arrival time at the sample between optical pulses comprising the pump beam 38 and corresponding optical pulses comprising the probe beam. If the second quarter wave plate 16 is aligned with its fast axis at an angle $\Psi$ to $\hat{y}$ (90°–$\psi$ to $\hat{x}$), the Jones vector corresponding to the electric field transmitted by the polarizer is given by $$E_\phi = \frac{E(\hat{x}+\hat{y})}{2}[(\sin^2\psi + i\cos^2\psi + (1-i)\sin\psi\cos\psi)r - (\cos^2\psi + i\sin^2\psi + (1-i)\sin\psi\cos\psi)r']. \quad (1)$$

This equation can be used to calculate how the intensity at photodetector 21, proportional to $|E_\psi|^2$, varies with the change $\delta r = r'-r$ in the complex amplitude reflection coefficient of the sample 14.

Figure 2:
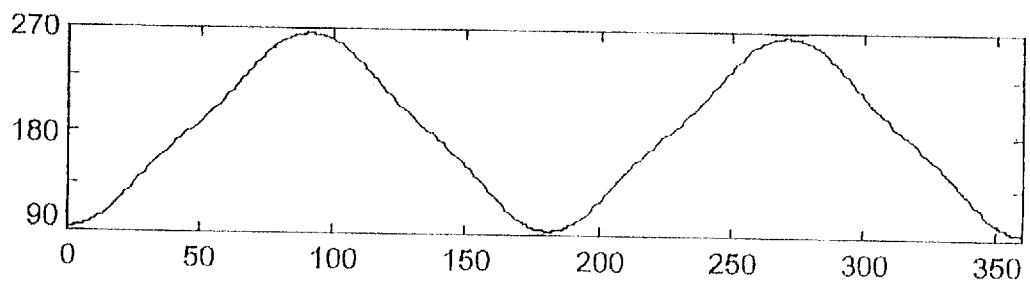
FIG. 2 is a graph showing phase difference in degrees between the probe and reference beams after transmission through the polarizer plotted as a function of the angle $\psi$ of the second quarter wave plate.
Figure 3:
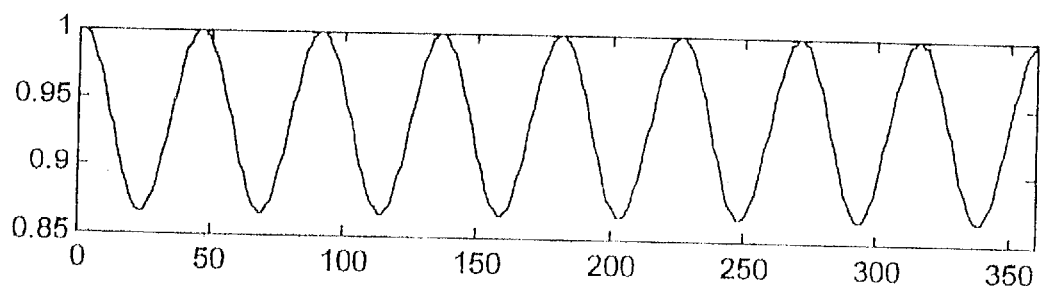
FIG. 3 is a graph showing fringe visibility plotted as a function of the angle $\psi$ of the second quarter wave plate.
Figure 4:
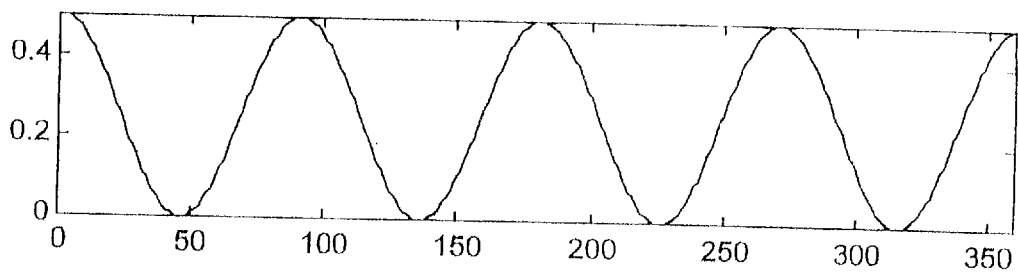
FIG. 4 is a graph showing total intensity of the second output beam at the photodetector normalized to that before the polarizer, plotted as a function of the angle $\psi$ of the second quarter wave plate.

The interferometer characteristics as a function of the angle $\psi$, obtained from $E_\psi$ or $|E_\psi|^2$, are illustrated in FIGS. 2–4. For the case r'=r exp(i$\delta\phi$), where $\delta\phi$ is a variable phase, we show in FIG. 2 the phase difference between the probe and reference components of the electric field after the polarizer for the case $\delta\phi=0$, in FIG. 3 the fringe visibility, and in FIG. 4 the total transmitted intensity for the case $\delta\phi=0$.

The maximum interferometric sensitivity, fringe visibility and intensity at the detector are simultaneously achieved with $\psi=0$, 90, 180, and 270 degrees. It is an important advantage of this embodiment that a fringe visibility at or near the maximum value of 1 can be obtained for this Sagnac interferometer.

With the angle $\psi$ set at 0 and 90 degrees, for example, Eq. (1) reduces, respectively, to $$E_0 = \frac{E(\hat{x}+\hat{y})}{2}[ir + (r + \delta r))]. \quad (2)$$

$$E_{90} = \frac{E(\hat{x}+\hat{y})}{2}[r - i(r + \delta r))]. \quad (3)$$

If we define $r=r_0 \exp[i\phi_0]$ and $r'=(r_0+\delta r_0)\exp[i(\phi_0+\delta\phi)]$, where $r_0$ is the optical amplitude reflection coefficient of the reference pulse, $\phi_0$ is the optical phase of the reference pulse, $\delta r_0$ is the change in the optical amplitude reflection coefficient induced by the pump pulse as probed by the probe pulse, and $\delta\phi$ is the change in the optical phase induced by the pump pulse as probed by the probe pulse.

Eqs. (2) and (3) then imply that the $\psi=0$ and $\psi=90$ degree outputs of the photodetector are respectively proportional to $$I_0 \approx E^2[\delta r_0^2 + 2r_0\delta r_0(1+\sin\delta\phi) + 2r_0^2 \sin\delta\phi], \quad (4)$$

$$I_{90} \approx E^2[\delta r_0^2 + 2r_0\delta r_0(1-\sin\delta\phi) - 2r_0^2 \sin\delta\phi]. \quad (5)$$

Eqs. (4) and (5) show that measurements simultaneously sensitive to both phase and intensity changes of the light reflected from the sample 14 can be made. Similar equations are obtained if the angle of the polarizer 17 is rotated by 90 degrees to be aligned in the direction $\hat{i}-\hat{y}$. Either position of the polarizer 17 can be used, provided that its axes are at 45 degrees to those of the second quarter wave plate 16.

Figure 5:
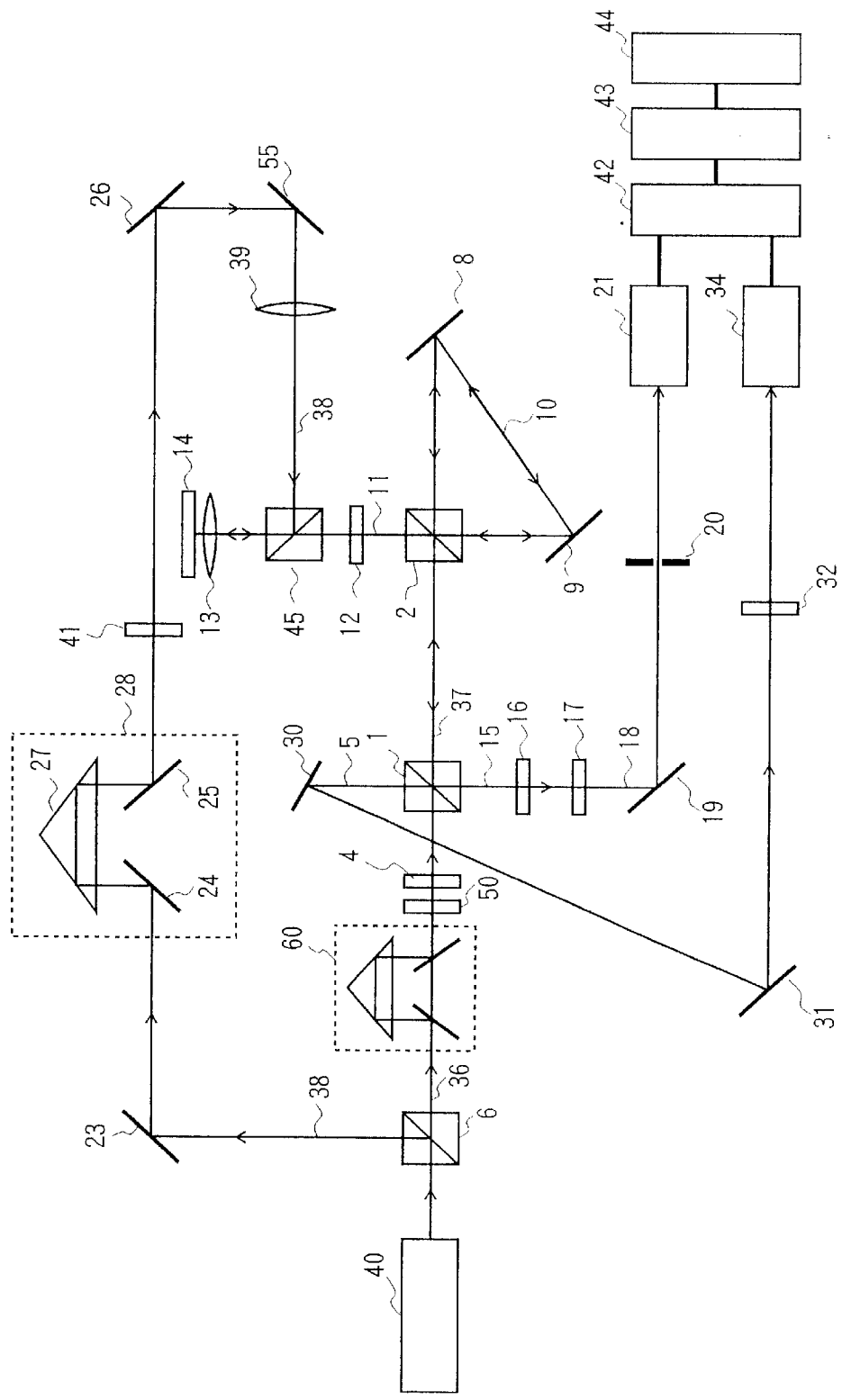
FIG. 5 is a diagram showing the configuration of a sample measurement apparatus according to a second embodiment of the invention, which apparatus uses a single-arm interferometer with two beam splitters. The pump and measurement beams have the same wavelength.

In another embodiment, shown in FIG. 5, the pump beam 38 and the measurement beam 36 have the same wavelength spectra. A chopper 50 is also placed in the path of measurement beam 36, so as to modulate at a different frequency from that of the chopper 41 in the pump beam 38. Signals at the difference or at the sum frequency of the two modulation frequencies are monitored at the lock-in amplifier 43. This method again allows a signal simultaneously depending on ultrafast changes in both phase and intensity of the light reflected from the sample 14 to be monitored. This modulation technique is particularly suitable when the wavelength spectra of the pump and measurement beams 38 and 36 are identical, because the detection at a different frequency from the pump modulation frequency avoids the problem of crosstalk from any stray light from the pump beam 38 reaching the photodetectors. This modulation technique is well known in the art of ultrashort pulse optical pump and probe techniques. The pump beam 38 and the recombined beam 11 can be combined with a non-polarizing beam splitter 45 to allow both beams to be normally incident on the sample 14. In this embodiment the second quarter wave plate 16 can also be placed at the input side of the interferometer, between polarizer 4 and the first beam splitter 1.

Another way of accomplishing the modulation of the measurement beam 36 is to modulate the angle $\psi$ in Eq. (1) by, for example, modulating the angle or orientation of the second quarter wave plate 16, or by replacing the second quarter wave plate 16 by a photoelastic modulator. For example one could choose $\psi=\psi_0+\psi_1\sin(2\pi ft)$, where $\psi_0$ and $\psi_1$, are constant phases and f is the modulation frequency. In this case, according to the Taylor expansion of the terms in Eq. (1), the relevant modulation frequency of the measurement beam 36 corresponds to f or some multiple of f.

Figure 6:
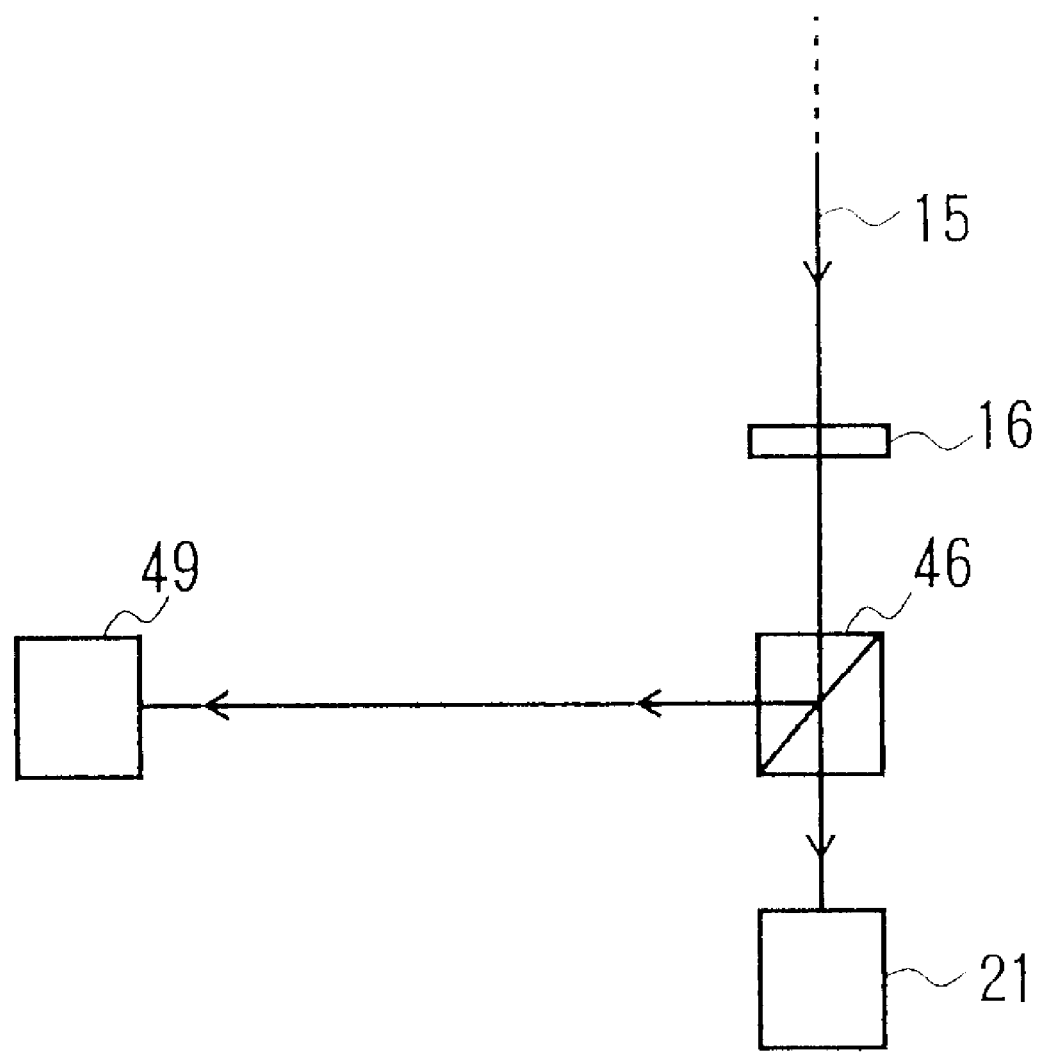
FIG. 6 is a diagram showing the configuration of an embodiment of the invention in which two different signals can be obtained simultaneously.

In another embodiment, part of which is shown in FIG. 6, an extra polarizing beam splitter 46 with its axes aligned at an angle of 45 degrees to the first beam splitter 1 is placed in the path of the first output beam 15 in order to split these beams into two parts. The first part of the beam split by the polarizing beam splitter 46 is incident on a first photodetector 21. The second part of the beam from the polarizing beam splitter 46 is incident on a second photodetector 49. In this way a signal at both the photodetectors is produced both corresponding either to a known phase difference of 90 degrees or both to a known phase difference of −90 degrees, and such that a signal at the second photodetector 49 responds with the opposite sign compared to the first photodetector 21 with respect to changes in phase of the measurement beam when reflected from the sample. This is well known in the art of interferometry. These two signals are effectively the same as those corresponding to the two Eqs. (4) and (5). This embodiment can be used in combination with a measurement beam sampling beam and another photodetector if it is desired to compensate for fluctuations in the intensity of the measurement beam. Alternatively, it is possible to obtain the difference of the signals at the two photodetectors 21 and 49 to extract the signal $$I_0 - I_{90} = 4E^2[r_0 \delta r_0 + r_0^2] \sin \delta\phi. \tag{6}$$

If changes in $\delta\phi$ and $\delta r_0$ are small, this quantity is proportional to $\delta\phi$, and a signal proportional to the change in phase $\delta\phi$ can be measured.

In another embodiment that can achieve a similar effect to the one shown in FIG. 6, the second quarter wave plate 16 is replaced by a photoelastic modulator that can produce a phase difference of either +90 degrees or −90 degrees between the probe and reference beams on passing through it. By switching between these two values, two signals, corresponding to Eqs. (4) and (5), can be obtained.

Figure 7:
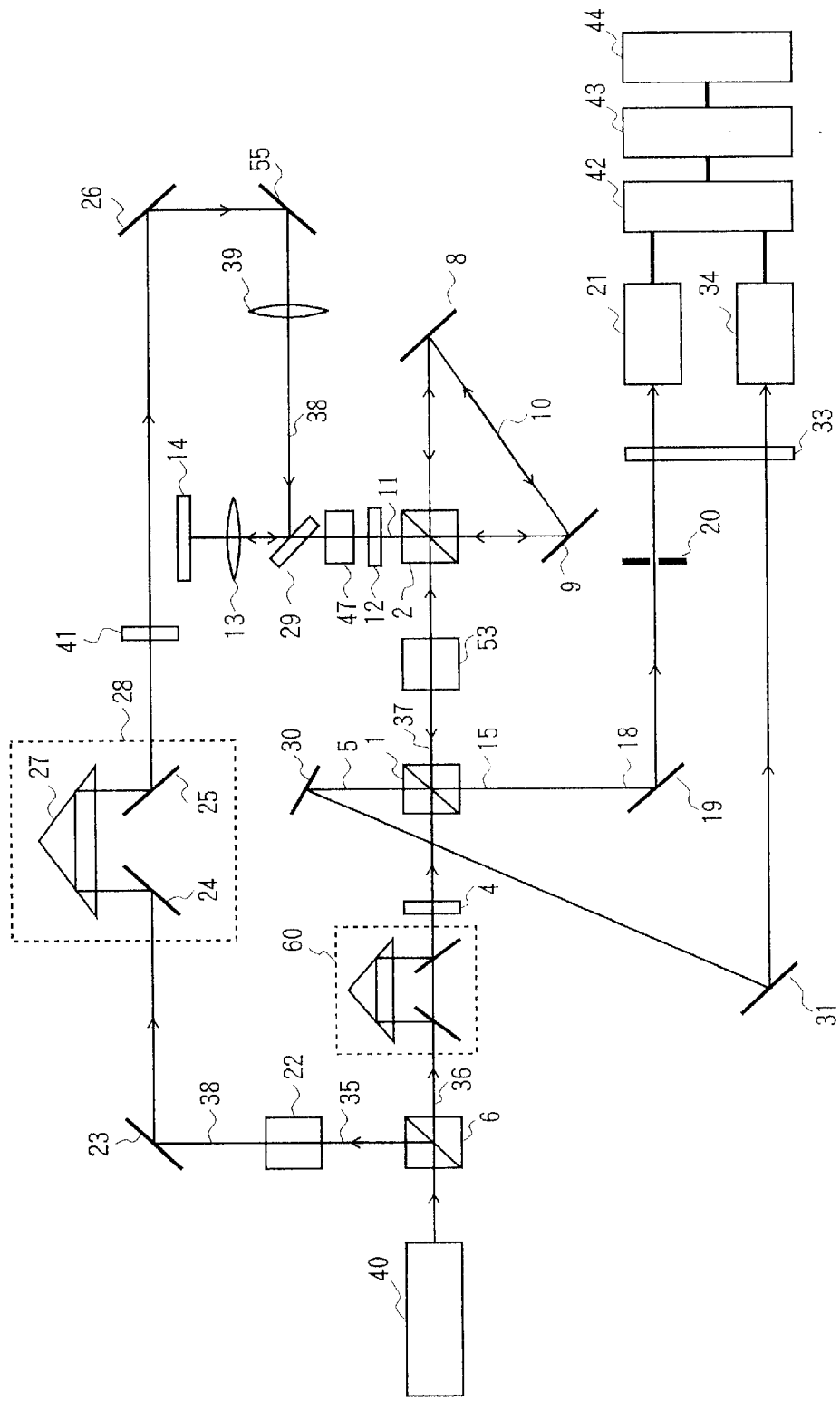
FIG. 7 is a diagram showing the configuration of an embodiment of the invention in which two Faraday rotators are used to reduce the loss in the interferometer.

In another embodiment, shown in FIG. 7, the first beam splitter 1 is chosen to be a polarizing beam splitter with its axes parallel to the second beam splitter 2, which is chosen to be a polarizing beam splitter. The axis of polarization of the measurement beam 36, when incident on the first beam splitter 1, can be chosen at some convenient angle to allow appropriate amounts of light to reach the two photodetectors 21 and 34. A 45 degree Faraday rotator 53 is placed between the first beam splitter 1 and the second beam splitter 2. The use of the Faraday rotator 53 allows the measurement beam 36 from the first beam splitter to be rotated by 45 degrees on first pass through it and by a further 45 degrees on the second pass through it after returning from reflection from the sample, to make a total of 90 degrees. In order to introduce a known phase difference of +90 degrees between corresponding radiation pulses in the reference beam and the probe beam a 22.5 degree Faraday rotator 47 is placed between the first quarter wave 12 plate and the sample 14. A second quarter wave plate is not used. Because the first beam splitter 1 now acts as a polarizer for the returning beam 37, no polarizer is required to be placed in the first output beam 15. The second output beam 18 is therefore interpreted here to be the same as the first output beam 15.

This embodiment therefore has the advantage that the intensity received at the photodetector 21 can be significantly increased because, in the ideal case, only half of the measurement beam intensity is lost when the probe and reference beams travel from the sample to the photodetector after reflection from the sample, whereas in the previous embodiments three quarters of the beam intensity is lost. The 22.5 degree Faraday rotator 47 can be chosen as a left-handed or right-handed rotator in order to correspond to a phase differences of +90 or −90 degrees between the reference and probe beams. The angle of the polarizer 4 can be adjusted to vary the intensity of the laser intensity sampling beam 5.

In another embodiment, for which the output of the radiation source is linearly polarized, the polarizer 4 can be replaced by a half wave plate to avoid loss.

In another embodiment only one photodetector 21 is used. In this case the measurement beam sampling beam 5 is not used.

In another embodiment, two radiation sources with trains of output pulses that are synchronous can be used for the pump and measurement beams. It is also possible to use two radiation sources with slightly different repetition rates in order to introduce a slowly varying ultrashort time-scale time delay between the pump and the measurement pulses, as is well known in the art.

Figure 8:
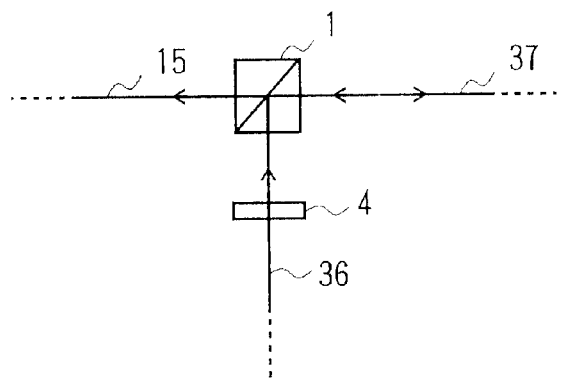
FIG. 8 is a diagram showing the configuration of an embodiment of the invention in which the measurement beam is reflected by 90 degrees when incident on the first beam splitter.

In another embodiment, part of which is shown in FIG. 8, the measurement beam 36 is reflected at 90 degrees from the first beam splitter 1, whereas the returning beam 37 is transmitted by the first beam splitter 1.

Figure 9:
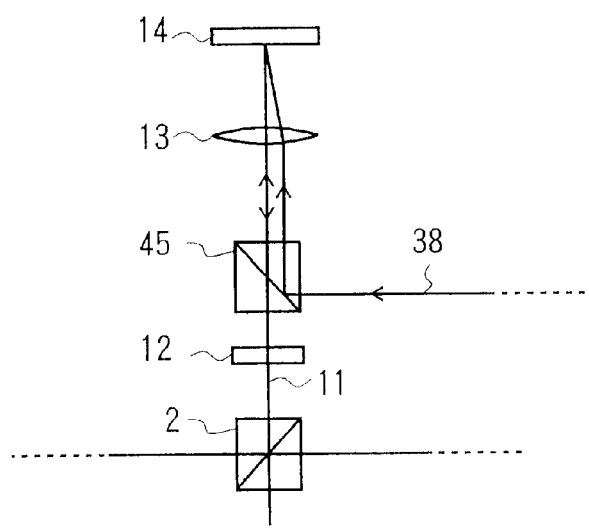
FIG. 9 is a diagram showing the configuration of an embodiment of the invention in which the pump beam is incident on the sample on the same side of the sample as the probe and reference beams at non-normal incidence using a beam splitter and the same means of focusing as the probe and reference beams.

In another embodiment, part of which is shown in FIG. 9, the pump beam 38 is incident on the sample 14 using the beam splitter 45 and the same means for focusing 13 on same side of the sample 14 as the probe and reference beams at non-normal incidence.

Figure 10:
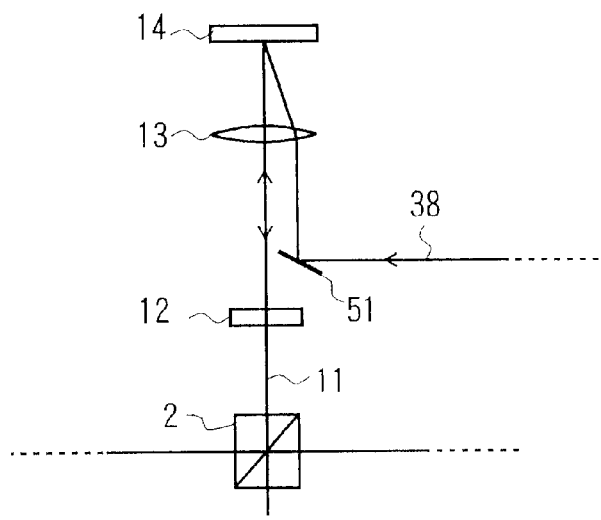
FIG. 10 is a diagram showing the configuration of an embodiment of the invention in which the pump beam is incident on the sample on the same side of the sample as the probe and reference beams at non-normal incidence using a mirror and the same means of focusing as the probe and reference beams.

In another embodiment, part of which is shown in FIG. 10, the pump beam 38 is incident on the sample 14 by means of a mirror 51 and the same means for focusing 13 on same side of the sample 14 as the probe and reference beams at non-normal incidence.

Figure 11:
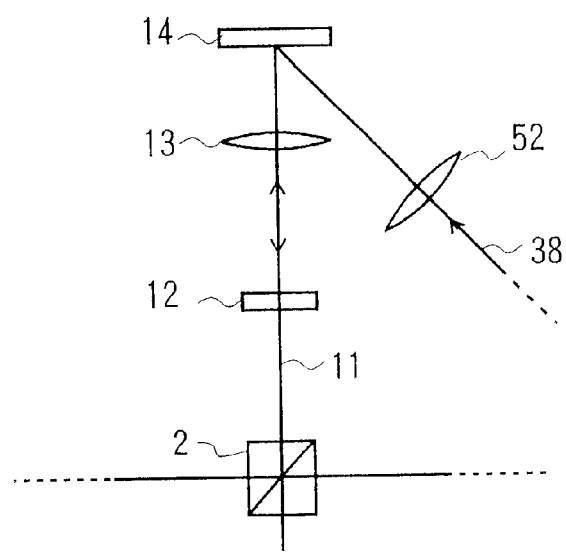
FIG. 11 is a diagram showing the configuration of an embodiment of the invention in which the pump beam is incident on the sample at non-normal incidence on the same side of the sample as the probe and reference beams using a different means of focusing from the probe and reference beams.

In another embodiment, part of which is shown in FIG. 11, the pump beam 38 is incident through a different means for focusing 52 on the same side of the sample 14 as the probe and reference beams at non-normal incidence.

Figure 12:
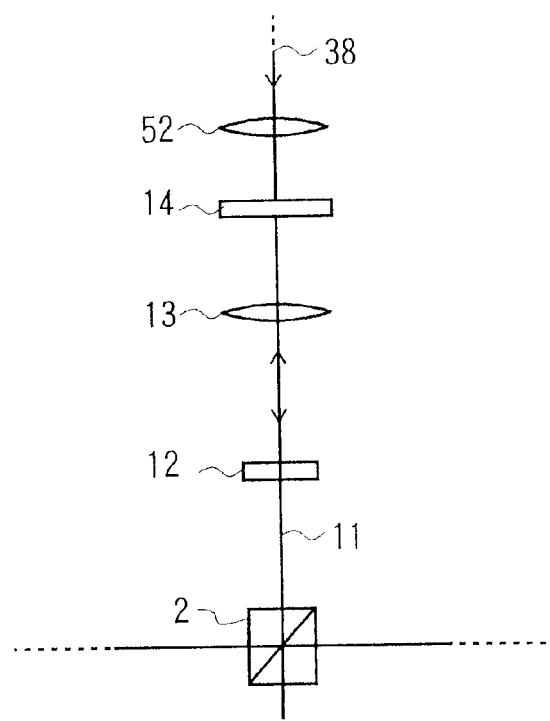
FIG. 12 is a diagram showing the configuration of an embodiment of the invention in which the pump beam is incident on the sample at normal or non-normal incidence on the opposite side of the sample as the probe and reference beams using a different means of focusing from the probe and reference beams.

In another embodiment, part of which is shown in FIG. 12, the pump beam 38 is incident through a different means for focusing 52 on the opposite side of the sample to the probe and reference beams at normal or non-normal incidence.

Figure 13:
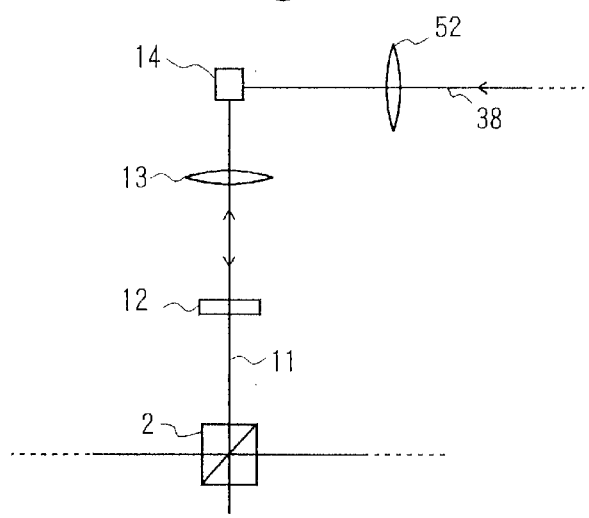
FIG. 13 is a diagram showing the configuration of an embodiment of the invention in which the pump beam is incident on the sample from a lateral direction using a different means of focusing from the probe and reference beams.

In another embodiment, part of which is shown in FIG. 13, the pump beam 38 is incident through a different means for focusing 52 from a lateral direction on the sample, not necessarily at 90 degrees to the direction of the recombined beam 11.

In another embodiment, the illuminated region of the sample 14 is scanned over the sample 14 by either moving the apparatus or by moving the sample 14, in order to spatially map the signal or signals simultaneously dependent on ultrafast changes in both phase and intensity of the light reflected from the sample 14. For a sample with a flat surface perpendicular to the direction of the recombined beam 11, this can be accomplished by scanning the sample 14 in the two lateral directions. In this embodiment, the pump beam 38 and the recombined beam 11 can be focused to the same point or different points, but their relative separation is fixed at some zero or non-zero value. The interval in arrival time at sample 14 between optical pulses comprising the pump beam 38 and corresponding optical pulses comprising the probe or reference beams can be fixed during this spatial scanning. Scans can be repeated for different intervals in arrival time to build up a complete temporal and spatial profile of the response of the sample 14.

In another embodiment, the region illuminated by the probe and reference beams is scanned with respect to the region illuminated by the pump beam 38, by relative movement of the recombined beam 11, the pump beam 38 and the sample 14, or a combination of these, in order to spatially map the signal or signals simultaneously dependent on ultrafast changes in both phase and intensity of the light reflected from the sample 14. A particular method to achieve this mapping is to keep the pump beam 38 and the sample 14 fixed with respect to one another, and then scan the recombined beam 11 laterally with respect to the sample 14. Another method is to keep the recombined beam 11 and the sample 14 fixed with respect to one another and to scan the position of the pump beam 38. Using the apparatus of the embodiment of FIG. 1, for example, this could be done by varying the angle of incidence of the pump beam 38 on the means for focusing 13. The interval in arrival time at sample 14 between optical pulses comprising the pump beam 38 and corresponding optical pulses comprising the probe or reference beams can be fixed during this spatial scanning. Scans can be repeated for different intervals in arrival time to build up a complete temporal and lateral spatial profile of the response of the sample 14. This method allows the investigation of the propagation of stress pulses or thermal waves in the lateral direction, for example, and measurement of corresponding physical properties corresponding to the in-plane direction in the sample. This would be useful, for example, with anisotropic samples. Examples of such stress waves are Lamb waves, Rayleigh waves, Love waves or Stoneley waves. For anisotropic samples, it is possible to use cylindrical lenses to generate stress waves with linear wave fronts, as is known in the art of acoustic microscopy. That is, by using a line-shaped optical spot, a stress wave having a line-shaped wave front is generated, and variation in the state of propagation of the stress wave, which depends the angle between the line-shaped optical spot and the axes of the sample is investigated. More generally, the propagation of stress waves or thermal waves in arbitrary directions in the sample will affect the temporal and lateral spatial profile of the response of the sample, and such three dimensional propagation can also be investigated. By measuring the lateral propagation of stress waves in combination with their propagation in the through-thickness direction, the sound velocities of different modes of elastic wave propagation could be obtained, allowing a greater number of elastic constants of the sample to be derived. This method also implies the possibility of the simultaneous measurement of film thickness and sound velocity without a separate calibration.

In another embodiment, corresponding optical pulses comprising the probe beam and those comprising the reference beam are chosen to both arrive after the pump beam 38. In this embodiment the difference in the ultrafast response of the sample 14 at two particular delay times can be monitored. For example, by choosing the interval between the arrival times at the sample of corresponding optical pulses comprising the probe beam and those comprising the reference beam to be relatively small, a signal or signals proportional to the derivative with respect to time of the ultrafast sample response can be obtained.

In another embodiment, the interval in arrival time at the sample between corresponding radiation pulses comprising the pump beam 38 and those comprising the reference beam is varied, and at the same time, the interval in arrival time at the sample between corresponding radiation pulses comprising the pump beam 38 and those comprising the probe beams is varied.

In general one or all of the intervals in arrival time at the sample between corresponding optical pulses comprising any of the pump beam 38, the probe beam and the reference beam can be fixed.

In general, some or all of the system components are realized with one, some or all of the following: fiber optics, micro-optics, integrated optics, conventional optics.

Also, it is possible, at the expense of a poorer signal-to-noise ratio, to replace the means for focusing 13 or means for focusing 52 by a near-field optical element such as a tapered optical fiber in order to improve the lateral spatial resolution.

The signals representative of the simultaneous ultrafast changes in both phase and intensity of the light reflected from the sample 14 arise from the mechanical motion of the surface of the sample 14 or of interfaces in the sample 14 and can also arise from changes in optical constants of the sample 14. This mechanical motion and these changes in optical constants arise from stress pulse generation and propagation in the sample 14 as well as from temperature changes, and there are in general also contributions from carrier excitation, relaxation and diffusion. These signals, dependent on physical properties of each part of the sample 14 such as thickness, sound velocity, elastic constants or thermal properties, can be used to measure these physical properties. Related quantities that affect such physical properties, such as ion implantation dose, can also be monitored. In the case of a multilayer sample, the properties of different layers can be simultaneously measured. Signals representative of the simultaneous ultrafast changes in both phase and intensity of the light reflected from the sample also depend on the presence of ejectant from the sample or irreversible transformation of the sample in the case when the optical pulses interact with the sample destructively. Such signals can also be used to probe physical properties of the sample.

The apparatus of the present invention could equally well be applied to samples that are made up of a combination of opaque, transparent or semitransparent parts. In addition, the apparatus could equally well be applied to samples made up of liquid, solid, gel-like or other components.

Specific examples will now be described.

Figure 14:
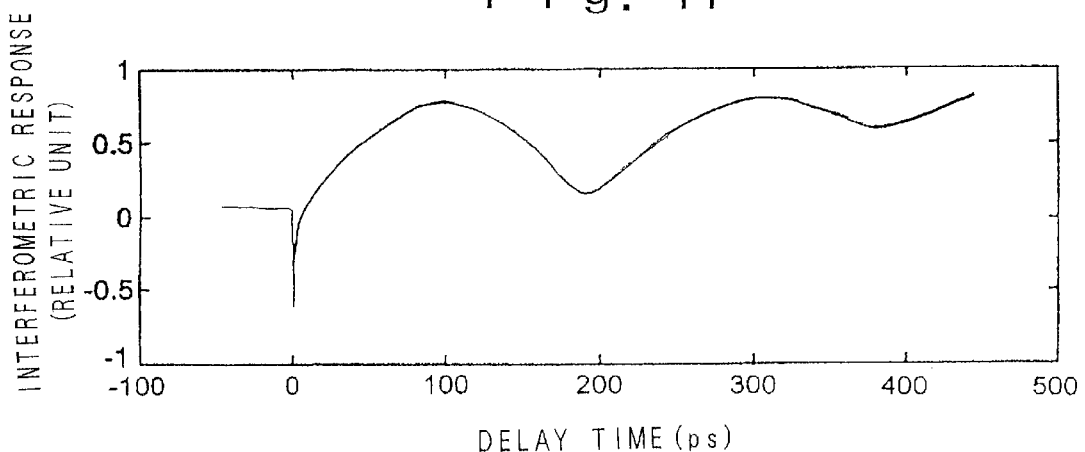
FIG. 14 is a graph showing the interferometric response $I_0$ for $\psi=0$ degrees for a gold film of thickness 330 nm on a silica substrate as a function of delay time between the pump and probe pulses, using the apparatus according to the first embodiment of the invention.
Figure 15:
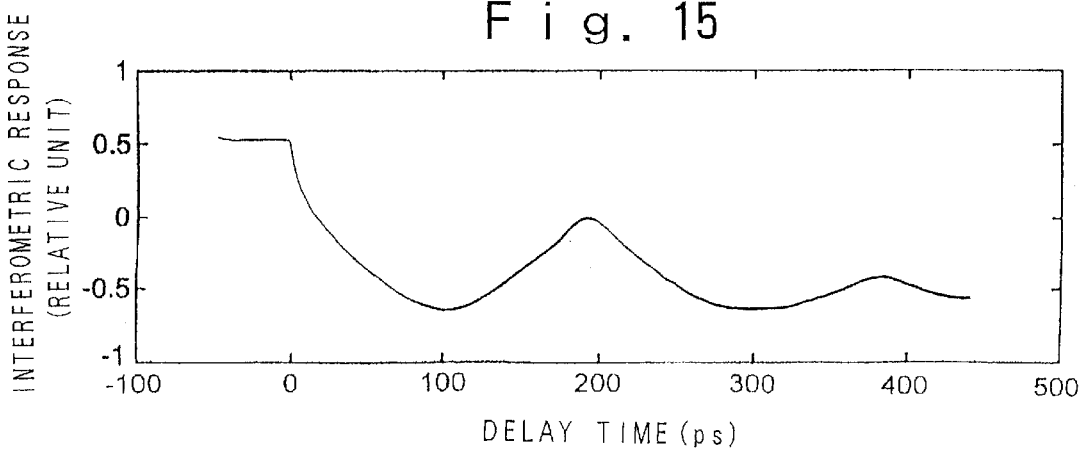
FIG. 15 is a graph showing the interferometric response $I_{90}$ for $\psi=90$ degrees for a gold film of thickness 330 nm on a silica substrate as a function of delay time between the pump and probe pulses, using the apparatus according to the first embodiment of the invention.

To test the characteristics of the apparatus we set up the embodiment as shown in FIG. 1. The pump and measurement pulse trains are derived from the same femtosecond Ti:sapphire laser with 100 fs pulse duration and 82 MHz repetition rate. The 830 nm output is used for the measurement beam 36, whereas the second harmonic at 415 nm is used for the pump beam 38. These two wavelengths are combined with a dichroic beam splitter to allow all the beams to pass through the same ×50 microscope objective used as the means for focusing 13, and produce a 2 $\mu$m diameter spot on the sample. The pump beam 38 is modulated with an acousto-optic modulator (at 1 MHz). A spatial filter 20 was not used. As a sample 14, an opaque polycrystalline gold thin film was prepared by evaporation on a silica substrate. FIGS. 14 and 15 show the two interferometric responses, $I_0$ and $I_{90}$, for an incident pump fluence of 0.5 mJ/cm$^2$ and probe fluence 0.1 mJ/cm$^2$, as a function of the delay time $\tau$, that is the interval in arrival time at sample 14 between optical pulses comprising the pump beam 38 and corresponding optical pulses comprising the probe beam. $I_0$ and $I_{90}$ respectively correspond to the angle $\psi=0°$ and 90° of the axis of the quarter wave plate 16. An important feature of the signals is the initial thermal expansion of the surface, producing an initial rise in the signal up to $\tau \approx 100$ ps, followed by two acoustic echoes at $\tau \approx 190$ and 380 ps arising from the propagation of longitudinal stress pulses in the through-thickness direction and their reflection from the film-substrate interface. In this example these expansion and acoustic echo signals in both FIGS. 14 and 15 arise almost entirely from the mechanical motion of the sample surface and not from changes in the optical constants of the film. This implies that variations in the optical phase $\delta\phi$ dominate the signal in this case. As is well known in the art of ultrasonics, the interval in time between acoustic echoes $\Delta\tau$ can be used to estimate the film thickness using the relation $d=v\Delta\tau/2$, where v is the longitudinal sound velocity of the film. Using the known longitudinal sound velocity of polycrystalline gold, $v=3360$ ms$^{-1}$, we find that d=320 nm. The shape of the echoes is known to be strongly influenced by electron diffusion, but this does not affect the method for determining the film thickness.

The amplitude of the signal depends on the thermal expansion coefficient of the sample, and so by scanning the sample in the lateral direction it is possible to obtain information about spatial variations in the thermal expansion coefficient.

In the case of gold the effect of variations in optical constants due to changes in sample temperature is relatively small compared to the effect of mechanical motion. However, in the general case, sample temperature changes dependent on thermal diffusion can be easily detected, and thermal properties such as the thermal diffusivity of the sample or of the components of the sample can be measured.

The apparatus could equally well be applied to samples that are made up of a combination of opaque, transparent or semitransparent parts. In addition, the apparatus could equally well be applied to samples made up of liquid, solid, gel-like or other components.

The apparatus could equally well be applied to generate and detect stress pulses in multilayer thin film samples and used to determine, for example, the thicknesses or elastic constants of the multilayer components.

The present invention is not limited to the above-described embodiment. Numerous modifications and variations of the present invention are possible in light of the spirit of the present invention, and they are not excluded from the scope of the present invention.

As described in detail, the present invention achieves the following advantageous effects.

The simple and robust apparatus described in this invention should be very effective in a wide range of applications for the measurement of properties of materials on short length scales in the direction perpendicular to the sample surface. Its versatility and stability should allow it to be applied to a variety of samples, samples that may be made up of a combination of opaque, transparent or semitransparent parts. The detection is inherently simultaneously sensitive to changes in both phase and intensity of the light reflected from the sample, allowing a maximum of information to be extracted.

This approach leads to a wider range of applications than methods only sensitive to the intensity of the light reflected from the sample. For example, for samples and optical wavelengths at which the changes in optical constants of the sample are negligible, the present apparatus can still detect signals due to the mechanical motion of the sample. The apparatus can monitor the properties of materials on short length scales by methods such as the generation and propagation of short wavelength stress pulses or thermal waves. Related physical properties can be mapped with a high lateral spatial resolution, determined only by the size of the illuminated region on the sample. Lateral scanning allows, for example, the investigation of the propagation of stress pulses or thermal waves in the lateral direction, and the measurement of corresponding physical properties corresponding to the in-plane direction in the sample. This would be useful, for example, with anisotropic samples.

The common path design of the interferometer is essential to minimize the effects of spurious mechanical vibrations or temperature changes. The combination of simultaneous sensitivity to changes in both phase and intensity together with the possibility of normal incidence of the probe and reference beams focused to a circular diffraction-limited spots is a great advantage of the method.

The use of normal incidence for the probe and reference beams, and the possible use of a single microscope objective for focusing all the optical beams on the sample at normal incidence are also very attractive features for a variety of non-destructive testing applications. Samples consisting of one or more layers or consisting of a material with a buried permanent inhomogeneity or inhomogeneities can be measured, and physical properties of the different layers or sections of the sample can be probed.

Moreover, the present invention can also be used to monitor the ejectant from a sample or the irreversible transformation of a sample when the interaction with the optical pump pulses is destructive. This has applications in the field of plasma diagnostics.

INDUSTRIAL APPLICABILITY

The apparatus for measuring physical properties of a sample according to the present invention can be applied to a wide range of measurement of physical properties such as thickness, sound velocity, and thermal properties of substances.

What is claimed is:

1. Apparatus for measuring physical properties of a sample, comprising:

(a) a coherent or partially coherent radiation source for providing a pulsed measurement beam having at least one ultrashort optical pulse having a duration of 0.002 ps to 2 ns;

(b) a radiation source for providing a pump beam having at least one ultrashort optical pulse having a duration of 0.002 ps to 2 ns;

(c) first and second beam splitters, at least a part of said measurement beam traversing said first beam splitter or being reflected from said first beam splitter, and then at least a part of said measurement beam, when incident on a second beam splitter, being split into a probe beam travelling in a single arm of said apparatus, wherein said probe beam is recombined with the remaining part of said measurement beam split from said second beam splitter and serving as a reference beam, to form a recombined beam, said reference beam having a different state of polarization from said probe beam, and the optical path length of the arm being chosen to be longer than the spatial extent, in the direction of propagation of the light, of the optical pulses in said reference and probe beams;

(d) means for directing said recombined beam onto said sample at normal incidence, such that said reference beam reflected from said sample travels in said single arm of said apparatus in the opposite direction to that previously mentioned for said probe beam when it travels through said single arm of said apparatus, and such that said reference beam and probe beam are recombined at said second beam splitter to produce a returning measurement beam propagating in the opposite direction to that of said measurement beam when said measurement beam is initially incident on said second beam splitter; and such that said returning measurement beam is then reflected from said first beam splitter or traverses said first beam splitter so as to produce a first output beam containing said reference and probe beams, and such that said first output beam is not colinear with said measurement beam when said measurement beam is initially incident on said first beam splitter;

(e) means for directing said pump beam at said sample;

(f) means for varying the interval in arrival time at said sample between radiation pulses comprising said pump beam and corresponding radiation pulses comprising said reference beam;

(g) means for varying the interval in arrival time at said sample between corresponding radiation pulses comprising said probe and reference beams;

(h) means for ensuring that at least part of said reference and said probe beams making up said first output beam are resolved into the same polarization state to form a second output beam;

(i) means for introducing a known phase difference or known phase differences not equal to $0 \pm 180I$ degrees (I is an integer) between corresponding radiation pulses in said reference beam and said probe beam at a photodetector or photodetectors, such that the intensity of said second output beam is simultaneously sensitive to both phase and intensity changes of the light reflected from said sample; and (j) means for directing at least part of said second output beam to said photodetector or photodetectors to detect the intensity of said second output beam that is characteristic of the interference between said reference and said probe beams making up said second output beam, in order to produce a signal or signals representative of the changes induced in said sample by said pump beam, such that physical properties of the sample can be measured by relating them to this signal or signals.

2. Apparatus for measuring physical properties of a sample of claim 1, characterized by said signal or signals representative of the changes induced in said sample by said pump beam being caused by mechanical motion of the surface of said sample or of interfaces in said sample.

3. Apparatus for measuring physical properties of a sample of claim 1, characterized by said signal or signals representative of the changes induced in said sample by said pump beam being caused by simultaneous presence of mechanical motion of the surface of said sample or of interfaces in said sample, together with changes in optical constants of said sample.

4. Apparatus for measuring physical properties of a sample of claim 1, characterized by both said pump and measurement beams consisting of a periodic train of radiation pulses, and including means for averaging said signal or signals derived from said photodetector or photodetectors over a number of pulses.

5. Apparatus for measuring physical properties of a sample of claim 1, characterized by both said pump and measurement beams consisting of a periodic train of radiation pulses derived from a single radiation source, and including means for averaging said signal or signals derived from said photodetector or photodetectors over a number of pulses.

6. Apparatus for measuring physical properties of a sample of claim 1, characterized by both said pump and measurement beams consisting of a periodic train of radiation pulses derived from different radiation sources, and including means for averaging said signal or signals derived from said photodetector or photodetectors over a number of pulses.

7. Apparatus for measuring physical properties of a sample of claim 1, further comprising means for modulating the intensity or polarization of either said pump beam or said measurement beam or said probe and reference beams, or a combination of these, and means for monitoring a signal or signals proportional to the amplitude of a modulated component or components of said signal or signals from said photodetector or photodetectors.

8. Apparatus for measuring physical properties of a sample of claim 7, in which two signals are used from said photodetector or photodetectors corresponding to phase differences of $90 \pm 360M$ degrees, where M is an integer, or $-90 \pm 360N$ degrees, where N is an integer, such that these two signals are obtained under the same or similar experimental conditions.

9. Apparatus for measuring physical properties of a sample of claim 8, in which two signals proportional to the amplitude of the appropriate components of the two modulated signals from said photodetectors are monitored.

10. Apparatus for measuring physical properties of a sample of claim 1, characterized by said pump beam being focused at non-normal incidence from the same side of said sample as said reference and said probe beams using some means for focusing.

11. Apparatus for measuring physical properties of a sample of claim 1, characterized by said pump beam being focused from the same side of said sample as the probe and reference beams, in which said pump beam is combined colinearly with said reference and said probe beams, and in which the same said means for focusing is then used to focus said pump beam from said sample at normal incidence.

12. Apparatus for measuring physical properties of a sample of claim 1, characterized by said pump beam being focused from the opposite side of said sample as said reference and said probe beams at normal or non-normal incidence using some means for focusing.

13. Apparatus for measuring physical properties of a sample of claim 1, characterized by said pump beam being focused from a lateral direction on said sample using some means for focusing.

14. Apparatus for measuring physical properties of a sample of claim 1, in which the interval in arrival times at said sample between corresponding radiation pulses comprising said pump beam and those comprising said probe beam is varied, and in which said signal or signals from said photodetector or photodetectors are monitored as a function of the corresponding interval in arrival times.

15. Apparatus for measuring physical properties of a sample of claim 1, in which the interval in arrival times at said sample between corresponding radiation pulses comprising said probe beam and those comprising said reference beam is varied, and in which said signal or signals from said photodetector or photodetectors are monitored as a function of the corresponding interval in arrival times.

16. Apparatus for measuring physical properties of a sample of claim 1, in which the interval in arrival time at said sample between corresponding radiation pulses comprising said pump beam and those comprising said reference beam is varied, and, at the same time, in which the interval in arrival time at said sample between corresponding radiation pulses comprising said probe beam and those comprising said reference beams is varied, and in which said signal or signals from said photodetector or photodetectors are monitored as a function of the corresponding intervals in arrival times.

17. Apparatus for measuring physical properties of a sample of claim 1, in which the interval in arrival time at said sample between corresponding radiation pulses comprising said pump beam and those comprising said reference beams is fixed.

18. Apparatus for measuring physical properties of a sample of claim 1, in which the interval in arrival time at said sample between corresponding radiation pulses comprising said probe beam and those comprising said reference beam is fixed.

19. Apparatus for measuring physical properties of a sample of claim 1, in which the interval in arrival time at said sample between corresponding radiation pulses comprising said pump beam and those comprising said reference beams is fixed, and, in addition, in which the interval in arrival time at said sample between corresponding radiation pulses comprising said probe beam and those comprising said reference beam is fixed.

20. Apparatus for measuring physical properties of a sample of claim 1, in which the illuminated region of said sample is scanned over said sample by either moving the apparatus or by moving said sample, in order to spatially map the physical properties of said sample.

21. Apparatus for measuring physical properties of a sample of claim 1, in which the region illuminated by said probe and reference beams is scanned with respect to the region illuminated by said pump beam, by relative movement of said probe and reference beams, said pump beam and said sample, or a combination of these, in order to spatially map the physical properties of said sample.

22. Apparatus for measuring physical properties of a sample of claim 1, characterized by said pump beam being used to excite from the same side of said sample as said reference and said probe beams, in which said pump beam has a different radiation wavelength spectrum from that of said probe and reference beams, and in which said pump beam is combined colinearly with said reference and said probe beams using a dichroic beam splitter or other beam splitter, and in which the same said means for focusing is used to focus said pump beam on said sample at normal incidence, and in which an optical filter is placed in front of said photodetector or photodetectors to prevent any light from said pump beam from reaching said photodetector or photodetectors.

23. Apparatus for measuring physical properties of a sample of claim 1, in which said signal or signals from said photodetector or photodetectors are subtracted from the signal or signals proportional to the intensity of said measurement beam.

24. Apparatus for measuring physical properties of a sample of claim 1, characterized in that said measurement beam is initially linearly polarized at an angle of 45 degrees to the axes of said first beam splitter, wherein said first beam splitter is a non-polarizing beam splitter;

said second beam splitter is a polarizing beam splitter with axes aligned parallel to said first beam splitter;

a first quarter wave plate is placed between said second beam splitter and said sample with its axes at 45 degrees to the axes of said second beam splitter in order to serve as a 90 degree polarization rotator for said reference and probe beams on passing through said first quarter wave plate twice;

these choices of system components allow that said probe beam travels in said single arm of said apparatus before being incident on said sample, and that said reference beam travels in said single arm of said apparatus in the opposite direction to that of said probe beam and does so after said reference beam is reflected from said sample;

said means for introducing said known phase difference between corresponding radiation pulses in said reference beam and said probe beam is a second quarter wave plate with its optical axes parallel to the axes of said beam splitters;

said second quarter wave plate is placed in the path of said first output beam or in the path of said measurement beam before said first beam splitter;

said means for ensuring that at least part of said reference and said probe beams making up said first output beam are resolved into the same polarization state to form a second output beam is a polarizer with its optical axis at 45 degrees to those of said second quarter wave plate;

said polarizer is placed in the path of said first output beam; and this combination of elements produces said known phase difference of ±90 degrees between corresponding radiation pulses in said reference beam and said probe beam.

25. Apparatus for measuring physical properties of a sample of claim 24, characterized in that an extra polarizing beam splitter is placed in the path of said first output beam after it has passed through the second quarter wave plate, in order to split this beam into two parts;

the axes of said extra polarizing beam splitter are at an angle of 45 degrees to those of the first beam splitter;

the first part of the beam split by said extra polarizing beam splitter is incident on a first photodetector;

the second part of the beam is incident on a second photodetector;

a signal at both said photodetectors is produced corresponding either to said known phase difference of 90 degrees or to said known phase difference of −90 degrees; and a signal at said second photodetector responds with the opposite sign compared to said first photodetector with respect to changes in phase of said measurement beam when reflected from said sample.

26. Apparatus for measuring physical properties of a sample of claim 1, characterized in that said measurement beam, when incident on the first beam splitter, is linearly polarized at a suitable angle to the axes of said first beam splitter, wherein said first beam splitter is a polarizing beam splitter;

said second beam splitter is a polarizing beam splitter with axes aligned parallel to said first beam splitter;

a 45 degree Faraday rotator is placed between said first beam splitter and said second beam splitter;

a first quarter wave plate is placed between said second beam splitter and said sample with its axes at 45 degrees to the axes of said beam splitters in order to serve as a 90 degree polarization rotator for said probe and reference beams on passing through said first quarter wave plate twice;

these choices of system components allow that said probe beam travels in said single arm of said apparatus before being incident on said sample, and that said reference beam travels in said single arm of said apparatus in the opposite direction to that of said probe beam and does so after said reference beam is reflected from said sample;

said means for introducing said known phase difference between corresponding radiation pulses in said reference beam and said probe beam is a 22.5 degree Faraday rotator placed between said first quarter wave plate and said sample;

said means for ensuring that at least part of said reference and said probe beams making up said first output beam are resolved into the same polarization state to form said second output beam is said first beam splitter; and this combination of elements produces said known phase difference of ±90 degrees between corresponding radiation pulses in said reference beam and said probe beam.

27. Apparatus for measuring physical properties of a sample of claim 1, characterized by the obtention of signals, at least part of which is representative of mechanical motion of the surface of said sample or of interfaces in said sample consisting of one or more layers or consisting of a material with a buried permanent inhomogeneity or inhomogeneities, owing to a stress pulse or stress pulses generated in said sample by said pump beam and subsequent propagation of these stress pulses and reflection of these stress pulses from the surface or interfaces of said sample, or reflection from a buried permanent inhomogeneity or inhomogeneities in said sample, in which said sample may be made up of opaque, transparent or semitransparent parts or a combination of these.

28. Apparatus for measuring physical properties of a sample of claim 27, characterized by the measurement of the thickness or sound velocity or both, or properties that affect the sound velocity, of at least one of the layers making up said sample consisting of one or more layers or of at least one of the sections of said sample defined by the buried permanent inhomogeneities.

29. Apparatus for measuring physical properties of a sample of claim 1, characterized by the obtention of several signals representing a stress pulse or stress pulses generated in said sample and subsequent propagation of these stress pulses and reflection of these stress pulses from the surface or interfaces of said sample, or reflection from a buried permanent inhomogeneity or inhomogeneities in said sample, owing to temperature changes and thermal diffusion generated in said sample by said pump beam, wherein said sample may be made up of opaque, transparent or semitransparent parts or a combination of these, and further characterized by the obtention of several signals representing mechanical motion of the surface of said sample or of interfaces in said sample consisting of one or more layers or consisting of a material with a buried permanent inhomogeneity or inhomogeneities.

30. Apparatus for measuring physical properties of a sample of claim 29, characterized by the measurement of the thickness or thermal properties, or properties that affect the thermal properties, of at least one of the layers making up said sample consisting of one or more layers or of at least one of the sections of said sample defined by the buried permanent inhomogeneities.

31. Apparatus for measuring physical properties of a sample of claim 1, characterized by the obtention of signals representative of the simultaneous presence of 1) mechanical motion of the surface of said sample or of interfaces in said sample consisting of one or more layers or consisting of a material with a buried permanent inhomogeneity or inhomogeneities; and 2) changes in optical constants of said sample, owing to temperature changes and thermal diffusion in said sample generated in said sample by said pump beam, in which said sample may be made up of opaque, transparent or semitransparent parts or a combination of these.

32. Apparatus for measuring physical properties of a sample of claim 31, characterized by the measurement of the thermal properties or thickness or both of at least one of the layers making up said sample consisting of one or more layers or of at least one of the sections of said sample defined by the buried inhomogeneities.

33. Apparatus for measuring physical properties of a sample of claim 29, characterized by the obtention of signals proportional to expansion or contraction of said sample surface.

34. Apparatus for measuring physical properties of a sample of claim 29, characterized by the measurement of thermal properties, or properties that affect the thermal properties, from expansion or contraction of said sample surface.

35. Apparatus for measuring physical properties of a sample of claim 1, characterized by the obtention of signals representative of the ejectant from said sample or from an irreversible transformation of said sample, owing to a destructive interaction of the optical pulses in said pump beam with said sample, in which said sample may be made up of opaque, transparent or semitransparent parts or a combination of these.

36. Apparatus for measuring physical properties of as sample of claim 35, characterized by the measurement of properties of said sample by their effect on the irreversible transformation.

37. Apparatus for measuring physical properties of a sample of claim 1, characterized by the angle of incidence of said recombined beam on said sample deviating slightly from normal incidence.

* * * * *

UNITED STATES PATENT AND TRADEMARK OFFICE
CERTIFICATE OF CORRECTION

PATENT NO. : 6,552,800 B1  Page 1 of 1
DATED : April 22, 2003
INVENTOR(S) : Wright et al.

It is certified that error appears in the above-identified patent and that said Letters Patent is hereby corrected as shown below:

Column 12,
Line 33, "$\tilde{x}$" should read -- $\hat{x}$ --.

Column 13,
Line 53, "+90" should read -- ± 90 --.

Column 17,
Line 36, "embodiment" should read -- embodiments --.

Column 24,
Line 40, "as" should read -- a --.

Signed and Sealed this

Second Day of December, 2003

JAMES E. ROGAN
*Director of the United States Patent and Trademark Office*